United States Patent [19]

Tully

[11] Patent Number: 4,588,720

[45] Date of Patent: May 13, 1986

[54] IMIDAZO[1,2-A]PYRIMIDINES

[75] Inventor: Wilfred R. Tully, Cirencester, Great Britain

[73] Assignee: Roussel Uclaf, Paris, France

[21] Appl. No.: 734,590

[22] Filed: May 15, 1985

Related U.S. Application Data

[62] Division of Ser. No. 526,046, Aug. 24, 1983, Pat. No. 4,532,243.

[30] Foreign Application Priority Data

Aug. 27, 1982 [GB] United Kingdom ............... 8224606
Feb. 9, 1983 [GB] United Kingdom ............... 8303612

[51] Int. Cl.⁴ ............... A61K 31/415; C07D 239/84; C07D 471/02
[52] U.S. Cl. ............... 514/217; 514/258; 544/250; 544/253; 544/281
[58] Field of Search ............... 544/250, 253; 514/267

[56] References Cited

U.S. PATENT DOCUMENTS

| | | | |
|---|---|---|---|
| 3,594,379 | 7/1971 | Hardtmann | 544/250 |
| 4,223,031 | 9/1980 | Covington et al. | 544/281 |
| 4,236,005 | 11/1980 | Dusza et al. | 544/281 |
| 4,374,988 | 2/1983 | Dusza et al. | 544/281 |
| 4,532,243 | 7/1985 | Tully | 544/281 |

Primary Examiner—Donald G. Daus
Assistant Examiner—Stephen M. Kapner
Attorney, Agent, or Firm—Bierman, Peroff & Muserlian

[57] ABSTRACT

Novel imidazo[1,2-a]pyrimidines of the formula

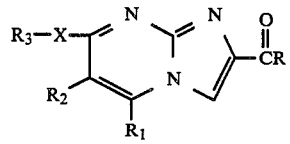

wherein R is selected from the group consisting of alkyl of 1 to 8 carbon atoms, alkenyl of 2 to 8 carbon atoms, cycloalkyl of 3 to 7 carbon atoms, cycloalkylalkyl of 4 to 12 carbon atoms, aryl of 6 to 12 carbon atoms, thienyl and pyridyl, each of said group being optionally substituted with at least one member of the group consisting of halogen, alkyl of 1 to 5 carbon atoms, alkoxy and alkylthio of 1 to 5 carbon atoms, trifluoromethyl, amino, alkylamino of 1 to 5 alkyl carbon atoms and dialkylamino with alkyl of 1 to 5 carbon atoms, $R_1$ and $R_2$ are individually selected from the group consisting of hydrogen, alkyl of 1 to 8 carbon atoms, alkenyl of 2 to 5 carbon atoms, cycloalkyl of 3 to 7 carbon atoms, cycloalkylalkyl of 4 to 12 carbon atoms, benzyl and phenethyl, or taken together form alkylene of 3 to 5 carbon atoms, each of said groups being optionally substituted with at least one member of the group consisting of halogen, alkyl of 1 to 5 carbon atoms, alkoxy and alkylthio of 1 to 5 carbon atoms, trifluoromethyl, amino, alkylamino of 1 to 5 alkyl carbon atoms and dialkylamino with alkyls of 1 to 5 carbon atoms, X is selected from the group consisting of oxygen and sulfur and $R_3$ is alkyl of 1 to 5 carbon atoms and their non-toxic, pharmaceutically acceptable acid addition salts, having anxiolytic activity and novel intermediates.

16 Claims, No Drawings

IMIDAZO[1,2-A]PYRIMIDINES

PRIOR APPLICATION

This application is a division of copending commonly assigned U.S. patent application Ser. No. 526,046 filed Aug. 24, 1983, now U.S. Pat. No. 4,532,243.

STATE OF THE ART

European patent application No. 0,061,380 describes imidazo[1,2-a]pyrimidines of the formula

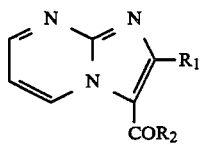

wherein $R_1$ and $R_2$ are alkyl, cycloalkyl or phenyl with 1 to 3 substituents or pyridyl or furyl or tetrahydrofuryl with at least one being a phenyl group having hypnotic activity.

OBJECTS OF THE INVENTION

It is an object of the invention to provide the novel imidazo[1,2-a]pyrimidines and their non-toxic, pharmaceutically acceptable acid addition salts and novel intermediates.

It is another object of the invention to provide novel anxiolytic compositions and to a novel method of inducing anxiolytic activity in warm-blooded animals.

These and other objects and advantages of the invention will become obvious from the following detailed description.

THE INVENTION

The novel compounds of the invention are imidzo[1,2-a]pyrimidines of the formula

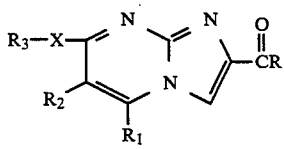

wherein R is selected from the group consisting of alkyl of 1 to 8 carbon atoms, alkenyl of 2 to 8 carbon atoms, cycloalkyl of 3 to 7 carbon atoms, cycloalkylalkyl of 4 to 12 carbon atoms, aryl of 6 to 12 carbon atoms, thienyl and pyridyl, each of said group being optionally substituted with at least one member of the group consisting of halogen, alkyl of 1 to 5 carbon atoms, alkoxy and alkylthio of 1 to 5 carbon atoms, trifluoromethyl, amino, alkylamino of 1 to 5 alkyl carbon atoms and dialkylamino with alkyl of 1 to 5 carbon atoms, $R_1$ and $R_2$ are individually selected from the group consisting of hydrogen, alkyl of 1 to 8 carbon atoms, alkenyl of 2 to 5 carbon atoms, cycloalkyl of 3 to 7 carbon atoms, cycloalkylalkyl of 4 to 12 carbon atoms, benzyl and phenethyl, or taken together form alkylene of 3 to 5 carbon atoms, each of said groups being optionally substituted with at least one member of the group consisting of halogen, alkyl of 1 to 5 carbon atoms, alkoxy and alkylthio of 1 to 5 carbon atoms, trifluoromethyl, amino, alkylamino of 1 to 5 alkyl carbon atoms and dialkylamino with alkyls of 1 to 5 carbon atoms, X is selected from the group consisting of oxygen and sulfur and $R_3$ is alkyl of 1 to 5 carbon atoms and their non-toxic, pharmaceutically acceptable acid addition salts.

Examples of alkyl of 1 to 8 carbon atoms, preferably of 1 to 5 carbon atoms, are methyl, ethyl, n-propyl, isopropyl, n-butyl, isobutyl, tert.-butyl, hexyl, heptyl, octyl and pentyl and examples of cycloalkyl are cyclopropyl, cyclobutyl, cyclopentyl, cyclohexyl and cycloheptyl. Examples of aryl of 6 to 12 carbon atoms are phenyl and naphthyl and examples of alkenyl of 2 to 5 carbon atoms optionally substituted by alkyl are vinyl, allyl, isopropenyl and but-3-enyl.

Examples of suitable acids for the formation of the non-toxic, pharmaceutically acceptable acid addition salts are inorganic acids such as hydrochloric acid, hydrobromic acid, hydroiodic acid, nitric acid, sulfuric acid, and phosphoric acid and organic acids such propionic acid, acetic acid, formic acid, maleic acid, benzoic acid, fumaric acid, succinic acid, tartaric acid, citric acid, oxalic acid, glyoxylic acid, aspartic acid, alkane sulfonic acid such as methane sulfonic acid and arylsulfonic acid such as benzene sulfonic acid or p-toluene sulfonic acid.

Among the preferred compounds of formula I are those wherein R is phenyl, those wherein $R_1$ and $R_2$ are individually hydrogen, methyl, ethyl, n-propyl, isopropyl, hexyl, allyl or benzyl, those wherein $R_3$ is methyl or ethyl and those wherein $R_1$ and $R_2$ are 1,3-propylene, 1,4-butylene, 1,5-pentylene or 2-methyl-1,4-butylene and their non-toxic, pharmaceutically acceptable acid addition salts.

Specific preferred compounds of formula I are [6-ethyl-5-methyl-7-(methylthio)imidazo[1,2-a]-pyrimidin-2-yl]phenylmethanone, (5-methoxy-6,7,8,9-tetrahydroimidazol[1,2-a]quinazolin-2-yl)-phenylmethanone; [5-(methylthio)cyclopenta[e]imidazol[1,2-a]pyrimidin-2-yl]-phenylmethanone; (7-methoxy-5-methyl-6-(1-methylethyl)imidazo[1,2-a]pyrimidin-2-yl]phenylmethanone; and (6-ethyl-7-methoxy-5-methylimidazo[1,2-a]pyrimidin-2-yl)phenylmethanone and their non-toxic, pharmaceutically acceptable acid addition salts.

The novel process of the invention for the preparation of the compounds of formula I comprises reacting a compound of the formula

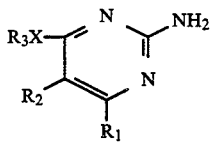

wherein $R_1$, $R_2$, $R_3$ and X have the above definition with a compound of the formula

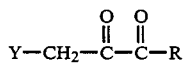

wherein R has the above definition and Y is a group capable of forming an anion $Y^\ominus$ to obtain a compound of the formula

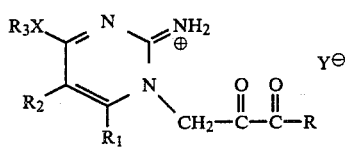

and cyclizing the latter to obtain the corresponding compound of formula I and optionally salifying the latter.

Preferably, the reaction of the compounds of formulae II and III is effected in an organic solvent such as ether, tetrahydrofuran or dimethoxyethane and the cyclization of the compound of formula IV with or without recovery is effected at reflux in a solvent such as methanol or stirring at room temperature in a solvent such as methanol in the presence of a base such as potassium carbonate. Generally, the cyclization results in a salt of the acid Y-H and the free base is easily obtained by reaction of the salt with a base such as an alkali metal hydroxide or carbonate such as potassium hydroxide or potassium carbonate. The free base may be optionally salified.

Some of the compounds of formula II are known in the literature and the new compounds may be prepared by the processes described in J.A.C.S., Vol. 81, (1959), p. 3108 or Rec. Trav. Chim., Vol. 61 (1942), p. 291 or Tetrahedron, Vol. 32 (1976), p. 1779. Some of the compounds of formula III are known and they may be prepared by the processes described in Helv. Chim. Acta., Vol. 29 (1846), p. 1247 or U.S. Pat. No. 2,821,555.

In a variation of the process of the invention to produce the compounds of formula I, a compound of formula II is reacted with a compound of the formula

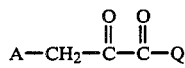

wherein A is a nucleophilic group and Q is an esterifying group to obtain a compound of the formula

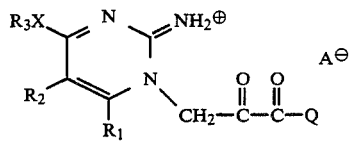

cyclizing the latter to obtain a compound of the formula

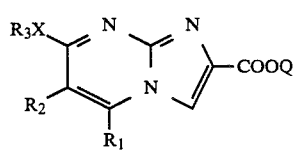

reducing the said product to obtain a compound of the formula

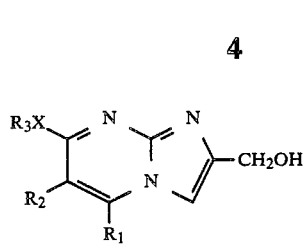

oxidizing the latter to obtain a compound of the formula

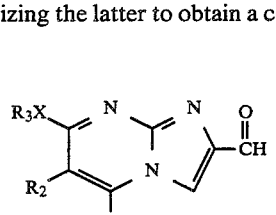

reacting the latter with a magnesium derivative of a compound of the formula

R—K   VII wherein R has the above definition and K is lithium or —MgHal and Hal is chlorine, bromine or iodine to obtain a compound of the formula

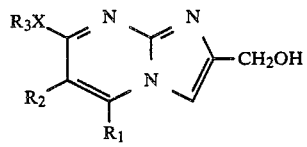

and oxidizing the latter to obtain the compound of formula I which may be salified if desired.

Preferably, the cyclization to obtain the compound of formula IX is effected under the same conditions as the product of formula IV and Q is alkyl or aralkyl especially alkyl of 1 to 3 carbon atoms such as ethyl. The reduction of the compound of formula IX is effected with lithium aluminium hydride or sodium borohydride in the presence of aluminium chloride or lithium borohydride. The oxidation of a compound of formula VIII is effected in a conventional manner such as with manganese dioxide although other oxidizing agents may be used. The reaction of compounds of formulae VI and VII is effected under anhydrous conditions in an organic solvent such as tetrahydrofuran and the oxidation of the compounds of formula V may be effected with manganese dioxide or with nitric acid, ferric chloride or chromic oxide in the presence of pyridine or by the Oppenauer method or by a dehydration in the presence of a catalyst based on copper.

Since the compounds of formula I have a basic character, they may be salified by reacting about stoichiometric amounts of the base and the acid with or without isolation of the base.

Certain of the compounds of formula IX are described in Farmaco, Ed. Sci., Vol. 32(10) (1977), p. 735 and Vol. 35(8) (1980), p. 654.

The novel anxiolytic compositions of the invention are comprised of an anxiolytically effective amount of at least one compound of formula I and its non-toxic, pharmaceutically acceptable acid addition salts and an inert pharmaceutical carrier or excipient. The compositions may be in the form of tablets, dragees, capsules, gelatin caspules, granules, suppositories or injectable solutions or suspensions prepared in the usual manner.

Examples of suitable excipients are talc, arabic gum, starch, lactose, magnesium stearate, cocoa butter, aqueous and non-aqueous vehicles, animal and vegetable fats, paraffinic derivatives, glycols, various wetting agents, dispersants and emulsifiers and/or preservatives.

Advantageously the compositions may be formulated as dosage units, each unit being adapted to supply a fixed dose of active ingredient. Suitable dosage units for adult human treatment may contain from 0.1 to 100 mg, preferably from 0.1 to 20 mg of active ingredient. The daily dosage will vary depending on the product employed, the subject to be treated and the condition, but will generally be in the range of 0.1 to 200 mg per day orally for adults.

The compositions of the invention are useful for the treatment of anxiety states such as chronic anxiety, accompanied by agitation, irritability or aggression, anxiety with insomnia and muscular tension and distress.

The novel method of invention for inducing anxiolytic activity in warm-blooded animals, including humans, comprises administering to warm-blooded animals an anxiolytically effective amount of at least one compound of formula I and their non-toxic, pharmaceutically acceptable acid addition salts. The compounds may be administered orally, rectally or parenterally and the usual daily dose is 0.015 to 2.8 mg/kg depending on the compound, the method of administration and the condition treated.

The compound of formula IV and compounds of formulae V, VI, VIII i.e. compounds of the formula

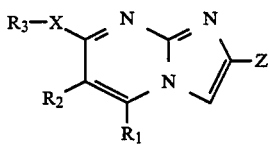

wherein $R_1$, $R_2$, $R_3$ and X are as hereinbefore defined and Z is —CHO or —CH(OH)R' wherein R' is hydrogen or R as defined above are also new compounds and constitutes a still further feature of the present invention.

In the following examples there are described several preferred embodiments to illustrate the invention. However, it should be understood that the invention is not intended to be limited to the specific embodiments.

EXAMPLE 1

(5-methoxy-6,7,8.9-tetrahydroimidazo[1,2-a]quinazolin-2-yl)phenylmethanone

A solution of 20 g of 4-methoxy-5,6,7,8-tetrahydro-2-quinazolinamine, 28.6 g of 3-bromo-1-phenyl-propane-1,2-dione and 400 ml of ether was stirred overnight at room temperature and was filtered. The 29.5 g of 4-methoxy-1-(3-phenyl-2,3-dioxopropyl)-5,6,7,8-tetrahydro-2-quinazolinium bromide were washed with ether and suspended in methanol. The suspension was refluxed for 2 hours and the solution was evaporated to dryness under reduced pressure. The residue was shaken with a mixture of aqueous potassium carbonate and chloroform and the decanted organic phase was washed with water, dried over magnesium sulfate and evaporated to dryness under reduced pressure. The residue was triturated with ethanol and filtered to obtain 18 g of (5-methoxy-6,7,8,9-tetrahydroimidazo[1,2-a]quinazolin-2-yl-phenylmethanone in the form of pale yellow crystals melting at 234° C.

EXAMPLES 2 TO 48

Using the procedure of Example 1, the appropriate compounds were reacted to obtain the compounds of Table I which lists the IR Spectrum, yield and melting point data. Table II gives the analytical data.

EXAMPLE 2

(5-Ethoxy-6,7,8,9-tetrahydroimidazo[1,2-a]quinazolin-2-yl)phenylmethanone.

EXAMPLE 3

(7-Methoxy-5-methylimidazol[1,2-a]pyrimidin-2-yl)-phenyl methanone.

EXAMPLE 4

(5-Methoxycyclopenta[e]imidazol[1,2-a]pyrimidin-2-yl)-phenylmethanone.

EXAMPLE 5

(5-Ethoxycyclopenta[e]imidazol[1,2-a]pyrimidin-2-yl)-phenylmethanone.

EXAMPLE 6

[5-(Methylthio)cyclopenta[e]imidazo[1,2-a]pyrimidin-2-yl]phenylmethanone.

EXAMPLE 7

(7-Methoxy-5,6-dimethylimidazo[1,2-a]pyrimidin-2-yl)phenylmethanone.

EXAMPLE 8

(5-Methoxycyclohepta[e]imidazo[1,2-a]pyrimidin-2-yl)phenylmethanone.

EXAMPLE 9

(6-Benzyl-7-methoxy-5-methylimidazo[1,2-a]pyrimidin-2-yl)phenylmethanone.

EXAMPLE 10

(5-Ethoxycyclohepta[e]imidazo[1,2-a]pyrimidin-2-yl)phenylmethanone.

EXAMPLE 11

(7-Methoxy-5-methyl-6-(1-methylethyl)imidazo[1,2-a]pyrimidin-2-yl)phenylmethanone.

EXAMPLE 12

[5-(Methylthio)-6,7,8,9-tetrahydroimidazo[1,2-a]quinazolin-2-yl]phenylmethanone.

EXAMPLE 13

[5-(Ethylthio)cyclopenta[e]imidazo[1,2-a]pyrimidin-2-yl]phenylmethanone.

EXAMPLE 14

(7-Methoxy-5-propylimidazo[1,2-a]pyrimidin-2-yl)phenylmethanone.

EXAMPLE 15

(5-Ethyl-7-methoxyimidazo[1,2-a]pyrimidin-2-yl)phenylmethanone.

EXAMPLE 16
(6-Ethyl-7-methoxy-5-methylimidazo[1,2-a]pyrimidin-2-yl)phenylmethanone.

EXAMPLE 17
(5-Methoxy-8-methyl-6,7,8,9-tetrahydroimidazo[1,2-a]quinazolin-2-yl]phenylmethanone.

EXAMPLE 18
[8-Methyl-5-(methylthio)-6,7,8,9-tetrahydroimidazo[1,2-a]quinzolin-2-yl]phenylmethanone.

EXAMPLE 19
(6-n-Hexyl-7-methoxy-5-methylimidazo[1,2-a]pyrimidin-2-yl)phenylmethanone.

EXAMPLE 20
(6-Allyl-7-methoxy-5-methylimidazo[1,2-a]pyrimidin-2-yl)phenylmethanone.

EXAMPLE 21
[5-Methyl-7-(methylthio)imidazo[1,2-a]pyrimidin-2-yl]phenylmethanone.

EXAMPLE 22
[7-(Methylthio)-5-propylimidazo[1,2-a]pyrimidin-2-yl]phenylmethanone.

EXAMPLE 23
[6-Cyclopropylmethyl-7-methoxy-5-methylimidazo[1,2-a]pyrimidin-2-yl]phenylmethanone.

EXAMPLE 24
[6-Cyclohexylmethyl-7-methoxy-5-methylimidazo[1,2-a]pyrimidin-2-yl]phenylmethanone.

EXAMPLE 25
[7-Ethoxy-6-ethyl-5-methylimidazo[1,2-a]pyrimidin-2-yl]phenylmethanone.

EXAMPLE 26
[7-Methoxy-6-methyl-5-propylimidazo[1,2-a]pyrimidin-2-yl]phenylmethanone.

EXAMPLE 27
[6-Ethyl-7-methoxy-5-n-propylimidazo[1,2-a]pyrimidin-2-yl]phenylmethanone.

EXAMPLE 28
[7-Methoxyimidazo[1,2-a]pyrimidin-2-yl]phenylmethanone.

EXAMPLE 29
[5-Ethyl-7-methoxy-6-methylimidazo[1,2-a]pyrimidin-2-yl]phenylmethanone.

EXAMPLE 30
[6-n-Butyl-7-methoxy-5-methylimidazo[1,2-]pyrimidin-2-yl]phenylmethanone.

EXAMPLE 31
[5,6-Diethyl-7-methoxyimidazo[1,2-a]pyrimidin-2-yl]phenylmethanone.

EXAMPLE 32
[7-Methoxy-5-methyl-6-n-propylimidazo[1,2-a]pyrimidin-2-yl]phenylmethanone.

EXAMPLE 33
[7-Methoxy-5,6-di-n-propylimidazo[1,2-a]pyrimidin-2-yl]phenylmethanone.

EXAMPLE 34
[6-n-Butyl-7-methoxy-5-n-propylimidazo[1,2-a]pyrimidin-2-yl]phenylmethanone.

EXAMPLE 35
[5-Ethyl-7-methoxy-6-n-propylimidazo[1,2-a]pyrimidin-2-yl]phenylmethanone.

EXAMPLE 36
[6-n-Butyl-5-ethyl-7-methoxy-imidazo[1,2-a]pyrimidin-2-yl]phenylmethanone.

EXAMPLE 37
[6-Allyl-7-methoxy-5-n-propylimidazo[1,2-a]pyrimidin-2-yl]phenylmethanone.

EXAMPLE 38
[6-Ethyl-7-methoxyimidazo[1,2-a]pyrimidin-2-yl]phenylmethanone.

EXAMPLE 39
[5-n-Butyl-7-methoxy-6-methylimidazo[1,2-a]pyrimidin-2-yl]phenylmethanone.

EXAMPLE 40
[7-Methoxy-6-n-propylimidazo[1,2-a]pyrimidin-2-yl]phenylmethanone.

EXAMPLE 41
[6-n-Butyl-7-methoxyimidazo[1,2-a]pyrimidin-2-yl]phenylmethanone.

EXAMPLE 42
[7-Methoxy-6-methylimidazo[1,2-a]pyrimidin-2-yl]phenylmethanone.

EXAMPLE 43
[5-n-Butyl-7-methoxyimidazo[1,2-a]pyrimidin-2-yl]phenylmethanone.

EXAMPLE 44
[6-Allyl-5-ethyl-7-methoxyimidazo[1,2-a]pyrimidin-2-yl]phenylmethanone.

EXAMPLE 45
[5-n-Butyl-6-ethyl-7-methoxyimidazo[1,2-a]pyrimidin-2-yl]phenylmethanone.

EXAMPLE 46
[5-n-Butyl-7-methoxy-6-n-propylimidazo[1,2-a]pyrimidin-2-yl]phenylmethanone.

EXAMPLE 47
[7-Methoxy-5-methyl-6-n-pentylimidazo[1,2-a]pyrimidin-2-yl]phenylmethanone.

EXAMPLE 48
[6-iso-Butyl-7-methoxy-5-methylimidazo[1,2-a]pyrimidin-2-yl]phenylmethanone.

TABLE 1

| Ex No | R | R₁ | R₂ | R₃X | Yield % | IR cm⁻¹ (KBr disc) | M.p. °C. |
|---|---|---|---|---|---|---|---|
| 1 | Ph | —(CH₂)₄— | | CH₃O | 52 | 3120,1640 | 234 |
| 2 | Ph | —(CH₂)₄— | | C₂H₅O | 48 | 3120,1640 | 250-2 |
| 3 | Ph | CH₃ | H | CH₃O | 43 | 3155,1650 | 165-6 |
| 4 | Ph | —(CH₂)₃— | | CH₃O | 35 | 3100,1655 | 210-1 |
| 5 | Ph | —(CH₂)₃— | | C₂H₅O | 47 | 3105,1640 | 227-9 |
| 6 | Ph | —(CH₂)₃— | | CH₃S | 44 | 3110,1640 | 208-9 |
| 7 | Ph | CH₃ | CH₃ | CH₃O | 76 | 3140,1650 | 198-205 |
| 8 | Ph | —(CH₂)₅— | | CH₃O | 44 | 3120,1630 | 196-8 |
| 9 | Ph | CH₃ | CH₂Ph | CH₃O | 55 | 3110,1640 | 199-202 |
| 10 | Ph | —(CH₂)₅— | | C₂H₅O | 39 | 3130,1640 | 193-4 |
| 11 | Ph | CH₃ | CH(CH₃)₂ | CH₃O | 48 | 3120,1640 | 148-50 |
| 12 | Ph | —(CH₂)₄— | | CH₃S | 35 | 3180,1639 | 225 |
| 13 | Ph | —(CH₂)₃— | | C₂H₅S | 63 | 3100,1630 | 211-2 |
| 14 | Ph | C₃H₇ | H | CH₃O | 37 | 3950,1640 | 152-4 |
| 15 | Ph | C₂H₅ | H | CH₃O | 49 | 3110,1640 | 179-82 |
| 16 | Ph | CH₃ | C₂H₅ | CH₃O | 68 | 3120,1640 | 148-50 |
| 17 | Ph | —CH₂CH(CH₃)CH₂CH₂— | | CH₃O | 43 | 3110,1640 | 200-1 |
| 18 | Ph | —CH₂CH(CH₃)CH₂CH₂— | | CH₃S | 52 | 3110,1630 | 215-7 |
| 19 | Ph | CH₃ | n-hexyl | CH₃O | 42 | 3130,1630 | 122-6 |
| 20 | Ph | CH₃ | CH₂=CHCH₂ | CH₃O | 68 | 3120,1640 | 128-31 |
| 21 | Ph | CH₃ | H | CH₃S | 58 | 3100,1640 | 170-2 |
| 22 | Ph | C₃H₇ | H | CH₃S | 72 | 3160,1650 | 162-3 |
| 23 | Ph | CH₃ | ▷—CH₂— | CH₃O | 32 | 3120,1640 | 136-7 |
| 24 | Ph | CH₃ | cyclohexyl-CH₂— | CH₃O | 55 | 3130,1645 | 169-70 |
| 25 | Ph | CH₃ | C₂H₅ | C₂H₅O | 23 | 3120,1640 | 154-9 |
| 26 | Ph | C₃H₇ | CH₃ | CH₃O | 40 | 3120,1640 | 140-1 |
| 27 | Ph | C₃H₇ | C₂H₅ | CH₃O | 36 | 3120,1635 | 122-3 |
| 28 | Ph | H | H | CH₃O | 84 | 3120,1640 | 209-9 |
| 29 | Ph | C₂H₅ | CH₃ | CH₃O | 31 | 3120,1641 | 174 |
| 30 | Ph | CH₃ | C₄H₉ | CH₃O | 26 | 3120,1640 | 141-5 |
| 31 | Ph | C₂H₅ | C₂H₅ | CH₃O | 23 | 3155,1642 | 141-2 |
| 32 | Ph | CH₃ | C₃H₇ | CH₃O | 54 | 3120,1640 | 141-2 |
| 33 | Ph | C₃H₇ | C₃H₇ | CH₃O | 31 | 3130,1640 | 123-4 |
| 34 | Ph | C₃H₇ | C₄H₉ | CH₃O | 30 | 3120,1635 | 113-4 |
| 35 | Ph | C₂H₅ | C₃H₇ | CH₃O | 26 | 3120,1635 | 151-2 |
| 36 | Ph | C₂H₅ | C₄H₉ | CH₃O | 20 | 3130,1635 | 158-9 |
| 37 | Ph | C₃H₇ | allyl | CH₃O | 40 | 3140,1640 | 122-3 |
| 38 | Ph | H | C₂H₅ | CH₃O | 52 | 3140,1650 | 126-9 |
| 39 | Ph | C₄H₉ | CH₃ | CH₃O | 14 | 3120,1640 | 122-4 |
| 40 | Ph | H | C₃H₇ | CH₃O | 89 | 3160,1625 | 137-9 |
| 41 | Ph | H | C₄H₉ | CH₃O | 48 | 3150,1660 | 149-50 |
| 42 | Ph | H | CH₃ | CH₃O | 32 | 3040,1660 | 179-80 |
| 43 | Ph | C₄H₉ | H | CH₃O | 39 | 3140,1650 | 170-1 |
| 44 | Ph | C₂H₅ | allyl | CH₃O | — | 3130,1640 | 130-1 |
| 45 | Ph | C₄H₉ | C₂H₅ | CH₃O | 17 | 3120,1640 | 124-5 |
| 46 | Ph | C₄H₉ | C₃H₇ | CH₃O | 19 | 3140,1640 | 118-9 |
| 47 | Ph | CH₃ | C₅H₁₁ | CH₃O | — | 3130,1640 | 150 |
| 48 | Ph | CH₃ | iso-C₄H₉ | CH₃O | 17 | 3130,1640 | 160 |

TABLE II

| Ex No | Formula | M. Wt. | Theory/Found C | H | N | X |
|---|---|---|---|---|---|---|
| 1 | C₁₈H₁₇N₃O₂(½H₂O) | 307.4 | 68.33 / 68.5 | 5.73 / 5.5 | 13.28 / 13.5 | |
| 2 | C₁₉H₁₉N₃O₂(½H₂O) | 321.4 | 69.07 / 69.3 | 6.10 / 5.9 | 12.72 / 12.8 | |
| 3 | C₁₅H₁₃N₃O₂ | 267.3 | 67.41 / 67.5 | 4.90 / 4.95 | 15.72 / 15.8 | |
| 4 | C₁₇H₁₅N₃O₂ | 293.3 | 69.61 / 69.8 | 5.15 / 5.2 | 14.33 / 14.5 | |
| 5 | C₁₈H₁₇N₃O₂ | 307.4 | 70.34 / 70.5 | 5.58 / 5.6 | 13.67 / 13.8 | |
| 6 | C₁₇H₁₅N₃OS | 309.4 | 66.00 / 65.95 | 4.89 / 5.0 | 13.58 / 13.6 | 10.36 (S) / 10.4 |
| 7 | C₁₆H₁₅N₃O₂ | 281.3 | 68.31 / 67.9 | 5.37 / 5.4 | 14.94 / 14.9 | |
| 8 | C₁₉H₁₉N₃O₂ | 321.4 | 71.01 / 70.9 | 5.96 / 6.0 | 13.07 / 13.1 | |
| 9 | C₂₂H₁₉N₃O₂ | 357.4 | 73.93 / 74.0 | 5.36 / 5.4 | 11.76 / 11.8 | |
| 10 | C₂₀H₂₁N₃O₂ | 335.4 | 71.62 / 71.65 | 6.31 / 6.4 | 12.53 / 12.5 | |
| 11 | C₁₈H₁₉N₃O₂ | 309.4 | 69.88 / 69.5 | 6.19 / 6.3 | 13.58 / 13.5 | |
| 12 | C₁₈H₁₇N₃OS(½H₂O) | 323.4 | 65.92 / 65.8 | 5.38 / 5.3 | 12.81 / 13.0 | 9.78 (S) / 9.85 |
| 13 | C₁₈H₁₇N₃OS | 323.4 | 66.85 / 66.8 | 5.30 / 5.3 | 12.99 / 13.0 | 9.91 (S) / 10.0 |
| 14 | C₁₇H₁₇N₃O₂ | 295.3 | 69.14 / 69.1 | 5.80 / 5.8 | 14.23 / 14.3 | |
| 15 | C₁₆H₁₅N₃O₂ | 281.3 | 68.31 / 68.3 | 5.37 / 5.4 | 14.94 / 15.0 | |
| 16 | C₁₇H₁₇N₃O₂ | 295.3 | 69.14 / 69.2 | 5.80 / 5.8 | 14.23 / 14.2 | |
| 17 | C₁₉H₁₉N₃O₂ | 321.4 | 71.01 / 71.1 | 5.96 / 6.0 | 13.07 / 13.0 | |
| 18 | C₁₉H₁₉N₃OS | 337.4 | 67.63 / 67.7 | 5.68 / 5.7 | 12.45 / 12.5 | 9.49 (S) / 9.4 |
| 19 | C₂₁H₂₅N₃O₂ | 351.2 | 71.77 / 71.8 | 7.17 / 7.1 | 11.96 / 11.9 | |
| 20 | C₁₈H₁₇N₃O₂ | 307.4 | 70.34 / 70.2 | 5.58 / 5.6 | 13.67 / 13.6 | |
| 21 | C₁₅H₁₃N₃OS | 283.4 | 63.61 / 63.5 | 4.62 / 4.7 | 14.83 / 14.8 | 11.32 (S) / 11.4 |
| 22 | C₁₆H₁₇N₃OS | 311.4 | 65.57 / 65.3 | 5.50 / 5.5 | 13.49 / 13.55 | 10.30 (S) / 10.4 |
| 23 | C₁₉H₁₉N₃O₂ | 321.4 | 71.01 / 71.0 | 5.96 / 6.0 | 13.07 / 13.1 | |
| 24 | C₁₉H₂₅N₃O₂ | 363.5 | 72.70 / 72.7 | 6.93 / 7.0 | 11.56 / 11.55 | |
| 25 | C₁₈H₁₉N₃O₂ | 309.4 | 69.88 / 69.7 | 6.19 / 6.2 | 13.58 / 13.5 | |
| 26 | C₁₈H₁₉N₃O₂ | 309.4 | 69.88 / 69.7 | 6.19 / 6.2 | 13.58 / 13.5 | |
| 27 | C₁₉H₂₁N₃O₂ | 323.4 | 70.57 / 70.6 | 6.55 / 6.5 | 12.99 / 13.0 | |
| 28 | C₁₄H₁₁N₃O₂ | 235.2 | 66.40 / 66.45 | 4.38 / 4.4 | 16.59 / 16.6 | |
| 29 | C₁₇H₁₇N₃O₂ | 295.3 | 69.14 / 69.0 | 5.80 / 5.8 | 14.23 / 14.0 | |
| 30 | C₁₉H₂₁N₃O₂ | 323.4 | 70.57 / 70.4 | 6.55 / 6.55 | 12.99 / 12.8 | |
| 31 | C₁₈H₁₉N₃O₂ | 309.4 | 69.88 / 69.6 | 6.19 / 6.3 | 13.58 / 13.4 | |
| 32 | C₁₈H₁₉N₃O₂ | 309.4 | 69.88 / 69.75 | 6.19 / 6.2 | 13.58 / 13.4 | |
| 33 | C₂₀H₂₃N₃O₂ | 337.4 | 71.19 / 71.1 | 6.87 / 6.95 | 12.45 / 12.4 | |
| 34 | C₂₁H₂₅N₃O₂ | 351.45 | 71.77 / 71.75 | 7.17 / 7.2 | 11.96 / 11.9 | |
| 35 | C₁₉H₂₁N₃O₂ | 323.4 | 70.57 / 70.4 | 6.55 / 6.55 | 12.99 / 13.0 | |
| 36 | C₂₀H₂₃N₃O₂ | 337.4 | 71.19 / 70.9 | 6.87 / 6.8 | 12.45 / 12.5 | |
| 37 | C₂₀H₂₁N₃O₂ | 335.4 | 71.62 / 71.7 | 6.31 / 6.3 | 12.53 / 12.5 | |
| 38 | C₁₆H₁₅N₃O₂ | 281.3 | 68.31 / 68.1 | 5.37 / 5.4 | 14.94 / 15.0 | |
| 39 | C₁₉H₂₁N₃O₂ | 323.4 | 70.57 / 70.2 | 6.55 / 6.4 | 12.99 / 13.0 | |
| 40 | C₁₇H₁₇N₃O₂ | 295.4 | 69.14 / 69.0 | 5.80 / 5.8 | 14.23 / 14.2 | |
| 41 | C₁₈H₁₉N₃O₂ | 309.4 | 69.88 / 69.8 | 6.19 / 6.2 | 13.58 / 13.6 | |
| 42 | C₁₅H₁₃N₃O₂ | 267.3 | 67.41 / 67.15 | 4.90 / 4.9 | 15.72 / 15.6 | |
| 43 | C₁₈H₁₉N₃O₂ | 309.4 | 69.88 / 69.5 | 6.19 / 6.2 | 13.58 / 13.4 | |
| 44 | C₁₉H₁₉N₃O₂ | 321.4 | | | | |
| 45 | C₂₀H₂₃N₃O₂ | 337.4 | 71.19 / 71.2 | 6.87 / 6.8 | 12.45 / 12.4 | |
| 46 | C₂₁H₂₅N₃O₂ | 351.45 | 71.77 / 71.8 | 7.17 / 7.2 | 11.96 / 11.9 | |
| 47 | C₂₀H₂₃N₃O₂ | 341.4 | 71.19 | 6.87 | 12.45 | |

TABLE II-continued

| Ex No | Formula | M. Wt. | Theory/Found C | H | N | X |
|---|---|---|---|---|---|---|
| 48 | $C_{19}H_{21}N_3O_2$ | 323.4 | 71.3<br>70.57<br>70.3 | 6.9<br>6.55<br>6.5 | 12.5<br>12.99<br>12.9 | |

EXAMPLE 49

[6-Ethyl-5-methyl-7-(methylthio)imidazo[1,2-a]pyrimidin-2-yl]phenylmethanone

A stirred suspension of 4.5 g of 5-ethyl-4-methyl-6-methylthio-2-pyrimidinamine in 28 ml of ether was treated with 5.5 g of 3-bromo-1-phenylpropane-1,2-dione to obtain a yellow solution. After standing two days at room temperature, the crystallized pyrimidinium salt was filtered off, washed with ether and heated for one hour in refluxing ethanol. The solution was evaporated to dryness under reduced pressure and the residue was shaken with a mixture of chloroform and aqueous potassium carbonate. The organic layer was washed, dried over $MgSO_4$ and evaporated to dryness under reduced pressure. Trituration of the residue with ethanol and filtration yielded 4.1 g (53% yield) of [6-ethyl-5-methyl-7-(methylthio)imidazo[1,2-a]pyrimidin-2-yl]phenylmethanone after recrystallization from methanol in the form of a buff solid.

EXAMPLES 50 TO 53

Using the method of Example 49, but starting from the corresponding compounds of formula II in which $R_1$, $R_2$, $R_3$ and X have the meanings indicated in Table III below, the compounds of Examples 50 to 53 were prepared IR Spectrum, yield and melting point data for the compounds are given in Table III and analytical data is given in Table IV.

EXAMPLE 50

[5-Methyl-7-(methylthio)-6-n-propylimidazo[1,2-a]pyrimidin-2-yl]phenylmethanone.

EXAMPLE 51

[6-Allyl-5-methyl-7-(methylthio)imidazo[1,2-a]pyrimidin-2-yl]phenylmethanone.

EXAMPLE 52

[5,6-Diethyl-7-(methylthio)imidazo[1,2-a]pyrimidin-2-yl]phenylmethanone.

EXAMPLE 53

[5-Ethyl-7-(methylthio)-6-n-propylimidazo[1,2-a]pyrimidin-2-yl]phenylmethanone.

TABLE III

| Ex. No. | R | $R_1$ | $R_2$ | $R_3$—X | Yield % | IRcm$^{-1}$ (KBr disc) | M.p. °C. |
|---|---|---|---|---|---|---|---|
| 49 | Ph | $CH_3$ | $C_2H_5$ | $CH_3$—S | 53 | 3120,1640 | 182–4 |
| 50 | Ph | $CH_3$ | $C_3H_7$ | $CH_3$—S | 33 | 3120,1640 | 146–7 |
| 51 | Ph | $CH_3$ | —$CH_2$—CH=$CH_2$ | $CH_3$—S | 45 | 3120,1635 | 167–9 |
| 52 | Ph | $C_2H_5$ | $C_2H_5$ | $CH_3$—S | 22 | 3110,1640 | 142–4 |
| 53 | Ph | $C_2H_5$ | $C_3H_7$ | $CH_3$—S | 24 | 3130,1645 | 156–8 |

TABLE IV

| Ex. No. | Formula | M. Wt. | Theory/Found C | H | N | S |
|---|---|---|---|---|---|---|
| 49 | $C_{17}H_{17}N_3OS$ | 311.4 | 65.57 | 5.50 | 13.49 | 10.30 |
| 50 | $C_{18}H_{19}N_3OS$ | 325.4 | 65.5<br>66.44<br>65.9 | 5.6<br>5.89<br>5.8 | 13.45<br>12.91<br>12.7 | 10.2<br>9.84<br>9.7 |
| 51 | $C_{18}H_{17}N_3OS$ | 323.4 | | | | |
| 52 | $C_{18}H_{19}N_3OS$ | 325.4 | 66.44<br>66.1 | 5.89<br>5.9 | 12.91<br>12.7 | 9.84<br>9.7 |
| 53 | $C_{19}H_{21}N_3OS$ | 339.5 | 67.23<br>66.9 | 6.24<br>6.1 | 12.38<br>12.2 | 9.44<br>9.3 |

EXAMPLE 54

(6-Ethyl-7-methoxy-5-methylimidazo[1,2-a]pyrimidin-2-yl)(4-methoxyphenyl)methanone

STEP A: Ethyl 6-ethyl-7-methoxy-5-methylimidazo[1,2-a]pyrimidine-2-carboxylate A solution of 50.1 g (0.3 mol) of 5-ethyl-4-methoxy-6-methyl-2-pyrimidinamine and 70.2 g (0.35 mol) of ethyl bromopyruvate in 300 ml of dry ether was stirred at room temperature for 24 hours and the precipitated white solid was collected by filtration, washed with ether and dried. The solid was suspended in 250 ml of ethanol and the stirred mixture was refluxed for 2 hours. The cooled solution was evaporated to dryness and the residue partitioned between chloroform and 5% sodium bicarbonate solution. The organic layer was separated and the aqueous layer was extracted with more chloroform. The organic extract was dried over anhydrous magnesium sulfate and evaporated to dryness under reduced pressure to obtain 6-ethyl-7-methoxy-5-methylimidazo[1,2-a]pyrimidine-2-carboxylate as a white crystalline solid which was purified by column chromatography on silica gel using a 7-3 chloroform/ethyl acetate mixture as the eluant. The 31.4 g of pure product (40% yield) was triturated with ethyl acetate/ether mixture, filtered, and dried in vacuo whereby it melted at 151°–2° C.

STEP B: (6-Ethyl-7-methoxy-5-methylimidazo[1,2-a]pyrimidin-2-yl)methanol 11.55 g (0.0525 mol) of lithium borohydride were added portionwise over 1 hour to a stirred solution of 19.7 g (75 mmol) of ethyl 6-ethyl-7-methoxy-5-methylimidazo[1,2-a]pyrimidine-2-carboxylate in 300 ml of dry tetrahydrofuran and after stirring at room temperature for 18 hours the excess borohydride was destroyed by dropwise addition of 300 ml of saturated sodium chloride solution. Then, the mixture was stirred for 30 minutes before separating the organic layer. The aqueous layer was extracted with chloroform and the combined extracts were dried over anhydrous magnesium sulfate and evaporated to dryness under reduced pressure to obtain 15.4 g of (6-ethyl-7-methoxy-5-methylimidazo[1,2-a]pyrimidin-2-yl)methanol (93% yield) as a white crystalline solid metling at 186°–188° C. (decomp.).

STEP C:
6-Ethyl-7-methoxy-5-methylimidazo[1,2-a]pyrimidine-2-carboxaldehyde To a solution of 15.25 g (69 mmol) of 6-ethyl-7-methoxy-5-methylimidazo-[1,2-a]pyrimidin-2-yl)methanol in 200 ml of chloroform was added 40 g of activated manganese dioxide and the stirred mixture was refluxed for 18 hours. A further 20 g of the oxidizing agent were added and the mixture was refluxed for a further 4 hours. The cooled mixture was filtered through celite and the filtrate was evaporated to obtain 10.9 g (72% yield) of 6-ethyl-7-methoxy-5-methylimidazo[1,2-a]pyrimidine-2-carboxaldehyde as a white crystalline solid melting at 185°–186° C.

Analysis: $C_{11}H_{13}N_3O_2$: Calculated: %C 60.26, %H 5.98, %N 19.17. Found: %C 60.0, %H 6.0, %N 19.05.

STEP D:
(6-Ethyl-7-methoxy-5-methylimidazo[1,2-a]pyrimidin-2-yl)(4-methoxyphenyl)methanol A solution of 4-methoxyphenylmagnesium bromide was prepared by treating 0.54 g (22.5 mg-atoms) of magnesium turnings with 4.20 g (22.5 mmol) of p-bromoanisole in 25 ml of dry tetrahydrofuran and was added dropwise to a stirred solution of 1.64 g (7.5 mmol) of 6-ethyl-7-methoxy-5-methylimidazo[1,2-a]pyrimidine-2-carboxaldehyde in 100 ml of dry tetrahydrofuran. After stirring at room temperature for 1 hour the mixture was poured into saturated ammonium chloride solution and the organic layer was separated. The aqueous layer was extracted with chloroform and the combined organic extracts were dried over $MgSO_4$ and evaporated to dryness under reduced pressure. The residue was deposited on a column of 250 g of silica gel and elution with a 7:3 chloroform-ethyl acetate mixture gave 2.3 g (94% yield) of (6-ethyl-7-methoxy-5-methylimidazo[1,2-a]pyrimidin-2-yl)(4-methoxyphenyl)methanol as a white crystalline solid melting at 117°–9° C.

STEP E:
(6-Ethyl-7-methoxy-5-methylimidazo[1,2-a]pyrimidin-2-yl)(4-methoxyphenyl)methanone 10 g of activated manganese dioxide were added to a solution of 2.2 g (6.7 mmol) of (6-ethyl-7-methoxy-5-methyl imidazo[1,2-a]pyrimidin-2-yl)(4-methoxyphenyl)methanol in 100 ml of chloroform and the mixture was stirred at room temperature for 18 hours. The mixture was filtered through celite and evaporation of the filtrate gave a solid product. Purification on a 100 g silica gel column using chloroform-methanol (98 to 2) as the eluant gave 1.3 g (59% yield) of pure (6-ethyl-7-methoxy-5-methylimidazo[1,2-a]pyrimidin-2-yl)(4-methoxyphenyl)methanone as a white crystalline solid melting at 196°–7° C. Overall yield from ester was 37%.

EXAMPLES 55 TO 76

Using the method of Example 54, but starting from the corresponding compounds of formula II in which $R_1$, $R_2$, $R_3$ and X have the meanings indicated in Table V below, the compounds of Examples 55 to 76 were prepared (see Table V below). IR Spectrum, yield, melting point, and analytical data for the compounds are also given in Table V.

EXAMPLE 54

(6-ethyl 7-methoxy 5-methylimidazo/1,2-a/pyrimidin-2-yl)(4-methoxyphenyl)methanone.

EXAMPLE 55

(6-ethyl 7-methoxy 5-methylimidazo/1,2-a/pyrimidin-2-yl)(4-chlorophenyl)methanone.

EXAMPLE 56

(6-ethyl 7-methoxy 5-methylimidazo/1,2-a/pyrimidin-2-yl)(4-methylphenyl)methanone.

EXAMPLE 57

(6-ethyl 7-methoxy 5-methylimidazo/1,2-a/pyrimidin-2-yl)(2-chlorophenyl)methanone.

EXAMPLE 58

(6-ethyl 7-methoxy 5-methylimidazo/1,2-a/pyrimidin-2-yl)(3-methoxyphenyl)methanone.

EXAMPLE 59

(6-ethyl 7-methoxy 5-methylimidazo/1,2-a/pyrimidin-2-yl)(4-methylthiophenyl)methanone.

EXAMPLE 60

6-ethyl 7-methoxy 5-methylimidazo/1,2-a/pyrimidin-2-yl(2-thienyl)methanone.

EXAMPLE 61

(6-ethyl 7-methoxy 5-methylimidazo/1,2-a/pyrimidin-2-yl)(2-pyridinyl)methanone.

EXAMPLE 62

(6-ethyl 7-methoxy 5-methylimidazo/1,2-a/pyrimidin-2-yl)(4-fluorophenyl)methanone.

EXAMPLE 63

(6-ethyl 7-methoxy 5-methylimidazo/1,2-a/pyrimidin-2-yl)/(3-trifluoromethyl)phenyl/methanone.

EXAMPLE 64

1-(6-ethyl 7-methoxy 5-methylimidazo/1,2-a/pyrimidin-2-yl)ethanone.

EXAMPLE 65

1-(6-ethyl 7-methoxy 5-methylimidazo/1,2-a/pyrimidin-2-yl)propanone.

EXAMPLE 66

1-(6-ethyl 7-methoxy 5-methylimidazo/1,2-a/pyrimidin-2-yl)butanone.

EXAMPLE 67

1-(6-ethyl 7-methoxy 5-methylimidazo/1,2-a/pyrimidin-2-yl)pentanone.

EXAMPLE 68

(6-ethyl 7-methoxy 5-methylimidazo/1,2-a/pyrimidin-2-yl/cyclopropyl methanone.

EXAMPLE 69

(5-ethyl 7-methoxy 5-methylimidazo/1,2-a/pyrimidin-2-yl)cyclopentyl methanone.

EXAMPLE 70

(6-ethyl 7-methoxy 5-methylimidazo/1,2-a/pyrimidin-2-yl)cyclohexyl methanone.

EXAMPLE 71

1-(6-ethyl 7-methoxy 5-methylimidazo/1,2-a/pyrimidin-2-yl)4-penten-1-one.

EXAMPLE 72

1-(6-ethyl 7-methoxy 5-methylimidazo/1,2-a/pyrimidin-2-yl)2-cyclohexyl ethanone.

EXAMPLE 73

(6-ethyl 7-methoxy 5-methylimidazo/1,2-a/pyrimidin-2-yl)1-naphtyl methanone.

EXAMPLE 74

(6-ethyl 7-methoxy 5-methylimidazo/1,2-a/pyrimidin-2-yl)(4-dimethylamino phenyl)methanone.

EXAMPLE 75

1-(6-ethyl 7-methoxy 5-methylimidazo/1,2-a/pyrimidin-2-yl)2-methyl 2-propen-1-one.

EXAMPLE 76

1-(6-ethyl 7-methoxy 5-methylimidazo/1,2-a/pyrimidin-2-yl)3-methyl butanone.

TABLE V

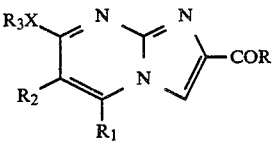

| Ex. | R | $R_1$ | $R_2$ | $R_3X$ | Yield | IR cm$^{-1}$ (KBr disc) | Mp | Formula | M. Wt | C | H | N | X |
|---|---|---|---|---|---|---|---|---|---|---|---|---|---|
| 54 | MeO—C$_6$H$_4$— | Me | Et | MeO | 37 | 3150, 1650 | 196–7 | $C_{18}H_{19}N_3O_3$ | 325.4 | 66.45 / 66.4 | 5.89 / 6.0 | 12.91 / 12.8 | |
| 55 | Cl—C$_6$H$_4$— | Me | Et | MeO | 48 | 3120, 1645 | 200–2 | $C_{17}H_{16}ClN_3O_2$ | 329.8 | | | | |
| 56 | Me—C$_6$H$_4$— | Me | Et | MeO | 49 | 3090, 1645 | 169–70 | $C_{18}H_{19}N_3O_2$ | 309.4 | 69.88 / 69.9 | 6.1 / 6.25 | 13.58 / 13.55 | |
| 57 | 2-Cl-C$_6$H$_4$— | Me | Et | MeO | 25 | 3140, 1650 | 218–20 | $C_{17}H_{16}ClN_3O_2$ | 329.8 | | | | |
| 58 | 3-MeO-C$_6$H$_4$— | Me | Et | MeO | 47 | 3170, 1635 | 149–50 | $C_{18}H_{19}N_3O_3$ | 325.4 | 66.45 / 66.5 | 5.89 / 5.95 | 12.91 / 12.8 | |
| 59 | MeS—C$_6$H$_4$— | Me | Et | MeO | 46 | 3130, 1645 | 201–2 | $C_{18}H_{19}N_3O_2S$ | 341.4 | | | | |
| 60 | thien-2-yl | Me | Et | MeO | 45 | 3130, 1640 | 206–8 | $C_{15}H_{15}N_3O_2S$ | 301.4 | 59.78 / 59.7 | 5.02 / 5.1 | 13.94 / 13.8 | S 10.64 / S 10.7 |
| 61 | pyridin-2-yl | Me | Et | MeO | 44 | 3180, 1645 | 211–3 | $C_{16}H_{16}N_4O_2$ | 296.3 | 64.85 / 64.7 | 5.44 / 5.5 | 18.91 / 18.85 | |
| 62 | F—C$_6$H$_4$— | Me | Et | MeO | 51 | 3120, 1645 | 182–4 | $C_{17}H_{16}FN_3O_2$ | 313.3 | | | | |

TABLE V-continued $$R_3X, R_2, R_1 \text{ substituted pyrimidine-COR structure}$$

| Ex. | R | $R_1$ | $R_2$ | $R_3X$ | Yield | IR cm$^{-1}$ (KBr disc) | Mp | Formula | M. Wt | Theory/Found C | H | N | X |
|---|---|---|---|---|---|---|---|---|---|---|---|---|---|
| 63 | F$_3$C-phenyl | Me | Et | MeO | 45 | 3130, 1645 | 170–2 | $C_{18}H_{16}F_3N_3O_2$ | 363.4 | 59.50 / 59.35 | 4.44 / 4.55 | 11.56 / 11.5 | F 15.69 / F 15.7 |
| 64 | Me | Me | Et | MeO | 45 | 3140, 1685 | 136–7 | $C_{12}H_{15}N_3O_2$ | 233.3 | 61.79 / 61.8 | 6.48 / 6.5 | 18.01 / 18.0 | |
| 65 | Et | Me | Et | MeO | 42 | 3130, 1680 | 184–5 | $C_{13}H_{17}N_3O_2$ | 247.3 | 63.14 | 6.93 | 16.99 | |
| 66 | Pr | Me | Et | MeO | 39 | 3140, 1680 | 150–1 | $C_{14}H_{19}N_3O_2$ | 261.3 | 64.35 / 64.15 | 7.33 / 7.3 | 16.08 / 16.0 | |
| 67 | Bu | Me | Et | MeO | 34 | 3130, 1680 | 157–8 | $C_{15}H_{21}N_3O_2$ | 275.4 | | | | |
| 68 | cyclopropyl | Me | Et | MeO | 36 | 3130, 1650 | 192–3 | $C_{14}H_{17}N_3O_2$ | 259.3 | 64.85 / 64.8 | 6.61 / 6.6 | 16.20 / 16.2 | |
| 69 | cyclopentyl | Me | Et | MeO | 20 | 3130, 1670 | 176–8 | $C_{16}H_{21}N_3O_2$ | 287.4 | 66.88 / 66.8 | 7.37 / 7.3 | 14.62 / 14.5 | |
| 70 | cyclohexyl | Me | Et | MeO | 34 | 3130, 1670 | 198–200 | $C_{17}H_{23}N_3O_2$ | 301.4 | 67.75 / 67.8 | 7.69 / 7.7 | 13.94 / 13.9 | |
| 71 | CH$_2$=CH(CH$_2$)$_2$ | Me | Et | MeO | 31 | 3130, 1675 | 163–5 | $C_{15}H_{19}N_3O_2$ | 273.3 | 65.91 / 65.6 | 7.01 / 6.9 | 15.37 / 15.3 | |
| 72 | cyclohexyl-CH$_2$- | Me | Et | MeO | 39 | 3140, 1670 | 177–9 | $C_{18}H_{25}N_3O_2$ | 315.4 | | | | |
| 73 | naphthyl | Me | Et | MeO | 33 | 3140, 1640 | 240–2 | $C_{21}H_{19}N_3O_2$ | 345.4 | | | | |
| 74 | Me$_2$N-phenyl- | Me | Et | MeO | 19 | 3130, 1640 | 221–3 | $C_{19}H_{22}N_4O_2$ | 338.4 | | | | |
| 75 | CH$_2$=CMe- | Me | Et | MeO | 35 | 3130, 1640 | 148–50 | $C_{14}H_{17}N_3O_2$ | 259.3 | | | | |
| 76 | Me$_2$CHCH$_2$- | Me | Et | MeO | 35 | 3130, 1675 | 139–40 | $C_{15}H_{21}N_3O_2$ | 275–4 | | | | |

EXAMPLE 77

Tablets were prepared in the usual manner containing 20 mg of the compound of Example 1 or Example 49 and sufficient excipient of talc, starch, lactose and magnesium stearate for a tablet weight of 150 mg.

PHARMACOLOGICAL DATA

A. Affinity for benzodiazepine receptors

The affinity of the compounds for benzodiazepine receptors was assessed using the radioligand [$^3$H] flunitrazepam and modifications of the original radioreceptor binding method of Squares and Braestrup (Nature, Vol. 266 (1977) p. 732). The values given in Table VI are nanomolar concentrations of test compound which inhibited the specific binding of 0.6 nM[$^3$H] flunitrazepam to rat forebrain membrain preparations by 50% (IC$_{50}$ nM).

B. Anxiolytic activity

Screening for anxiolytic activity was carried out by modifications of the conflict method of Geller and Seifter (Psychopharmacologia, (1960), Volume I, p. 482). The values given in Table VI are the minimum effective doses at which there was an observed increase in shocks above control (MED me/kg po).

TABLE V

| Example | Receptor Binding (IC$_{50}$nM) | Geller Conflict (MED mg/kg po) |
|---|---|---|
| 1 | 61 | 5 |
| 3 | 800 | 5 |
| 4 | 200 | 20 |
| 6 | 35 | 2 |
| 7 | 235 | 50 |
| 8 | 125 | 10 |
| 9 | 45 | 50 |
| 10 | 4000 | 5 |
| 11 | 37 | 2 |
| 12 | 8.5 | 10 |
| 13 | 1850 | 50 |
| 14 | 535 | 1 |
| 15 | 295 | 2 |
| 16 | 56 | 2 |
| 17 | 135 | 10 |
| 18 | 76 | 50 |
| 19 | 180 | 20 |
| 20 | 45 | 4 |
| 21 | 190 | 50 |
| 22 | 89 | 50 |
| 23 | 30 | 10 |
| 24 | 250 | 50 |
| 25 | 1900 | 50 |
| 26 | 740 | 20 |
| 27 | 470 | 50 |
| 28 | 8500 | 50 |
| 29 | 1000 | 20 |
| 30 | 42 | 2 |
| 31 | 107 | 2 |
| 32 | 85 | 5 |
| 33 | 1250 | 50 |
| 34 | 710 | 50 |
| 35 | 34 | 10 |
| 36 | 34 | 10 |
| 37 | 135 | 50 |
| 38 | 1500 | 5 |
| 39 | 400 | 50 |
| 40 | 1900 | 50 |
| 41 | 300 | 50 |
| 42 | 5900 | 50 |
| 43 | 340 | 10 |
| 44 | 42 | 10 |
| 45 | 500 | 50 |
| 46 | 1200 | 20 |
| 47 | 107 | 20 |
| 48 | 400 | 20 |
| 49 | 12 | 2 |
| 50 | — | — |
| 51 | — | — |
| 52 | 12 | — |
| 53 | 47 | — |
| 54 | 59 | 10 |
| 55 | 85 | 50 |
| 56 | 68 | 50 |
| 57 | 100 | 50 |
| 58 | 500 | 50 |
| 59 | 300 | 50 |
| 60 | — | 50 |
| 61 | — | 50 |
| 62 | — | 10 |
| 63 | — | 50 |
| 64 | — | 50 |

Various modifications of the products and methods of the invention may be made without departing from the spirit or scope thereof and it is to be understood that the invention is intend to be limited only as defined in the appended claims.

What I claim is:

1. A compound selected from the group consisting of imidazo[1,2-a]pyrimidines of the formula

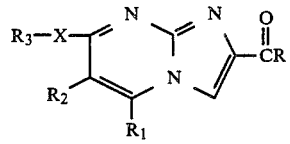

wherein R is selected from the group consisting of alkyl of 1 to 8 carbon atoms, alkenyl of 2 to 8 carbon atoms, cycloalkyl of 3 to 7 carbon atoms, cycloalkylalkyl of 4 to 12 carbon atoms, phenyl naphthyl, thienyl and pyridyl, each of said groups being optionally substituted with a member of the group consisting of halogen, alkyl of 1 to 5 carbon atoms, alkoxy and alkylthio of 1 to 5 carbon atoms, trifluoromethyl, amino, alkylamino of 1 to 5 alkyl carbon atoms and dialkylamino with alkyl of 1 to 5 carbon atoms, $R_1$ and $R_2$ taken together form alkylene of 3 to 5 carbon atoms optionally substituted with a member of the group consisting of halogen, alkyl of 1 to 5 carbon atoms, alkoxy and alkylthio of 1 to 5 carbon atoms, trifluoromethyl, amino, alkylamino of 1 to 5 alkyl carbon atoms and dialkylamino with alkyls of 1 to 5 carbon atoms, X is selected from the group consisting of oxygen and sulfur and $R_3$ is alkyl of 1 to 5 carbon atoms and their non-toxic, pharmaceutically acceptable acid addition salts.

2. A compound of claim 1 wherein R is phenyl.

3. A compound of claim 1 wherein $R_1$ and $R_2$ taken together form a member of the group consisting of 1,3-propylene, 1,4-butylene, 1,5-pentylene and 2-methyl-1,4-butylene and $R_3$ is methyl or ethyl.

4. A compound of claim 3 wherein R is phenyl.

5. A compound of claim 1 selected from the group consisting of (5-methoxy-6,7,8,9-tetrahydroimidazo[1,2-a]quinazolin-2-yl]phenylmethanone and its non-toxic, pharmaceutically acceptable acid addition salts.

6. A compound of claim 1 wherein R is selected from the group consisting of alkyl of 1 to 8 carbon atoms, cycloalkyl of 3 to 7 carbon atoms, cycloalkylalkyl of 4 to 12 carbon atoms, phenyl naphthyl, pyridyl and thienyl, $R_1$ and $R_2$ taken together form a straight chain alkylene of 3 to 5 carbon atoms optionally substituted with alkyl of 1 to 3 carbon atoms, each of R, $R_1$ and $R_2$ being optionally substituted with a member of the group consisting of halogen, alkyl of 1 to 5 carbon atoms and alkoxy of 1 to 5 carbon atoms.

7. A compound of the formula

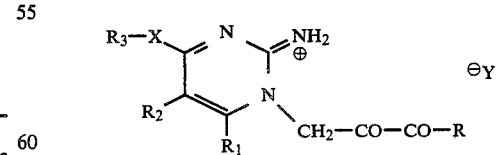

wherein R, $R_1$, $R_2$, $R_3$ and X are as defined in claim 1 and $Y^{\ominus}$ is an anion.

8. A compound of claim 7 wherein $Y^{\ominus}$ is a halide ion.

9. A compound of claim 7 wherein $Y^{\ominus}$ is a bromide ion.

10. A compound of the formula

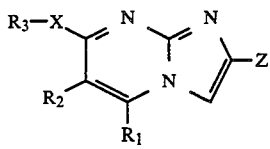

wherein $R_1$, $R_2$, $R_3$ and X are as defined in claim 1 and Z is —CHO or —CH(OH)R' and R' is hydrogen or R as defined in claim 1.

11. An anxiolytic composition comprising an anxiolytically effective amount of at least one compound of claim 1 and an inert pharmaceutical carrier.

12. A composition of claim 11 wherein R is phenyl.

13. A composition of claim 11 wherein $R_1$ and $R_2$ taken together form a member of the group consisting of 1,3-propylene, 1,4-butylene, 1,5-pentylene and 2-methyl-1,4-butylene and $R_3$ is methyl or ethyl.

14. A composition of claim 13 wherein R is phenyl.

15. A composition of claim 11 wherein the active compound is selected from the group consisting of (5-methoxy-6,7,8,9-tetrahydroimidazo[1,2-a]quinazolin-2-yl)phenylmethanone and its non-toxic, pharmaceutically acceptable acid addition salts.

16. A method of inducing anxiolytic activity in warm-blooded animals comprising administering to warm-blooded animals an anxiolytically effective amount of at least one compound of claim 1.

* * * * *